(12) United States Patent
Murayama et al.

(10) Patent No.: US 11,061,046 B2
(45) Date of Patent: Jul. 13, 2021

(54) LIQUID DELIVERY METHOD, LIQUID DELIVERY APPARATUS AND ANALYZER

(71) Applicant: KONICA MINOLTA, INC., Tokyo (JP)

(72) Inventors: Takanori Murayama, Tachikawa (JP); Youichi Aoki, Toda (JP)

(73) Assignee: KONICA MINOLTA, INC., Tokyo (JP)

( * ) Notice: Subject to any disclaimer, the term of this patent is extended or adjusted under 35 U.S.C. 154(b) by 474 days.

(21) Appl. No.: 15/762,074

(22) PCT Filed: Oct. 26, 2016

(86) PCT No.: PCT/JP2016/081694
§ 371 (c)(1),
(2) Date: Mar. 21, 2018

(87) PCT Pub. No.: WO2017/073601
PCT Pub. Date: May 4, 2017

(65) Prior Publication Data
US 2018/0292428 A1 Oct. 11, 2018

(30) Foreign Application Priority Data
Oct. 30, 2015 (JP) .............................. JP2015-214782

(51) Int. Cl.
*G01N 35/10* (2006.01)
*G01N 33/543* (2006.01)
*G01N 37/00* (2006.01)

(52) U.S. Cl.
CPC ....... *G01N 35/1011* (2013.01); *G01N 33/543* (2013.01); *G01N 33/54373* (2013.01);
(Continued)

(58) Field of Classification Search
None
See application file for complete search history.

(56) References Cited

U.S. PATENT DOCUMENTS

| 5,452,619 A * | 9/1995 | Kawanabe | G01N 33/491 |
| | | | 73/863 |
| 2003/0157503 A1* | 8/2003 | McGarry | B01L 3/502723 |
| | | | 435/6.11 |

(Continued)

FOREIGN PATENT DOCUMENTS

| JP | 2004061320 A | 2/2004 |
| JP | 2013185967 A | 9/2013 |

OTHER PUBLICATIONS

Machine Translation of JP2004-061320; provided in IDS submitted by applicant, translation generated May 5, 2020 (Year: 2004).*

(Continued)

*Primary Examiner* — Jill A Warden
*Assistant Examiner* — Brittany I Fisher
(74) *Attorney, Agent, or Firm* — Holtz, Holtz & Volek PC

(57) ABSTRACT

A liquid delivery method according to the present invention performs a procedure including supplying a first liquid into a microchannel and collecting the first liquid from within the microchannel, and then, dispensing a first amount of a second liquid without hermetically sealing a pipette tip insertion hole, then, dispensing a second amount of the second liquid in a state where the pipette tip insertion hole is hermetically closed to supply the second liquid into the microchannel.

19 Claims, 8 Drawing Sheets

(52) U.S. Cl.
CPC ......... *G01N 35/10* (2013.01); *G01N 35/1016* (2013.01); *G01N 37/00* (2013.01)

(56) References Cited

U.S. PATENT DOCUMENTS

| | | | | |
|---|---|---|---|---|
| 2004/0223874 | A1* | 11/2004 | Numajiri | B01L 3/502761 422/400 |
| 2006/0228263 | A1* | 10/2006 | Berndtsson | B01L 3/502715 422/514 |
| 2006/0263263 | A1* | 11/2006 | Shimizu | G01N 21/05 422/68.1 |
| 2007/0036679 | A1* | 2/2007 | Munenaka | B01L 3/502715 422/68.1 |
| 2007/0267335 | A1* | 11/2007 | Gao | B01D 19/00 210/120 |
| 2010/0068824 | A1* | 3/2010 | Kimura | G01N 21/648 436/501 |
| 2012/0156800 | A1* | 6/2012 | Aoki | G01N 21/648 436/180 |
| 2015/0165435 | A1* | 6/2015 | Chu | B01L 3/502784 435/7.9 |
| 2015/0352547 | A1* | 12/2015 | Breinlinger | B01L 3/5027 435/395 |

OTHER PUBLICATIONS

Machine Translation of JP2013-185967; provided in IDS submitted by applicant, translation generated May 5, 2020 (Year: 2013).*
English Translation of Written Opinion dated Jan. 17, 2017 issued in International Application No. PCT/JP2016/081694.
International Search Report (ISR) dated Jan. 17, 2017 issued in International Application No. PCT/JP2016/081694.
Written Opinion dated Jan. 17, 2017 issued in International Application No. PCT/JP2016/081694.

* cited by examiner

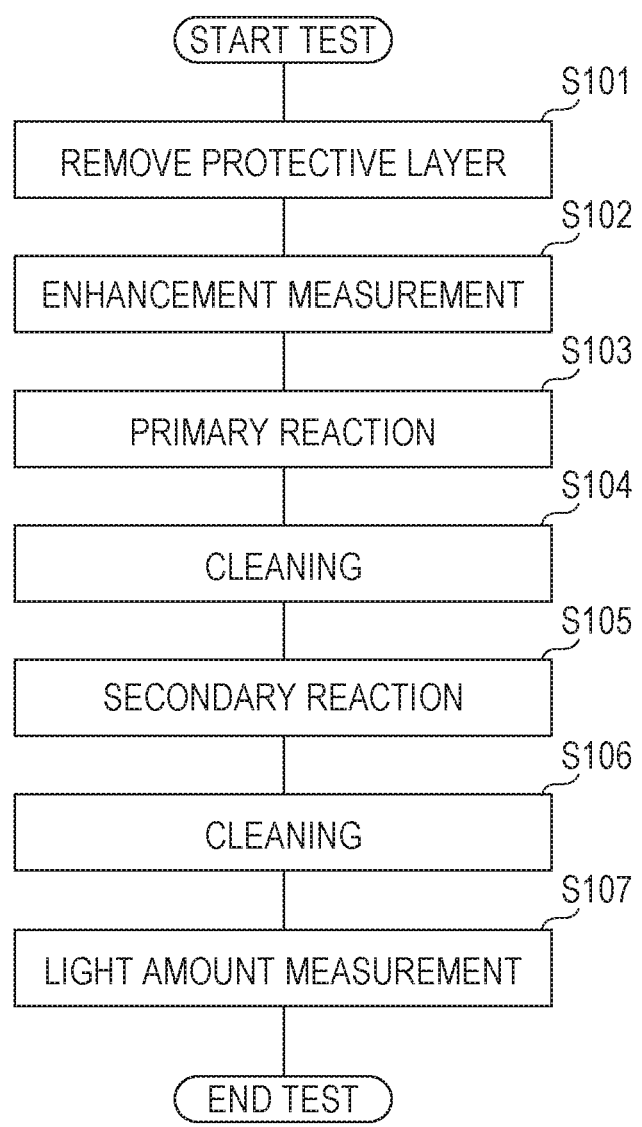

LIQUID DELIVERY METHOD, LIQUID DELIVERY APPARATUS AND ANALYZER

TECHNICAL FIELD

The present invention relates to a liquid delivery technique applied to supply a liquid to a microchannel in an analysis chip used in a biochemical testing apparatus.

BACKGROUND ART

Biochemical tests include the use of biochemical reactions such as an antigen-antibody reaction. These biochemical reactions are performed using an analysis chip or the like. The analysis chip includes a microchannel, within which an antigen capture membrane as a reaction field of a biochemical reaction is fixed. In advancing the reaction, a liquid sample containing the target antigen is supplied to the microchannel from one opening of the microchannel. A solid phase antibody to capture the target antigen is immobilized on the antigen capture membrane, and thus, filling the liquid sample in the microchannel brings the liquid sample into contact with the antigen capture membrane, allowing the target antigen to bind to the solid phase antibody to be captured. After a sufficient time has elapsed for the reaction, the liquid sample is collected from the microchannel, and then, the fluorescent labeling liquid is supplied to the microchannel. The fluorescent labeling liquid is filled in the microchannel to bring the fluorescent labeling liquid into contact with the antigen capture membrane, causing the target antigen captured by the antigen capture membrane to bind to the fluorescent labeling antibody contained in the fluorescent labeling liquid to be fluorescent-labeled. After a sufficient time for the reaction has elapsed, the fluorescent labeling liquid is collected from the microchannel to finish the reaction. Thereafter, the presence or absence, the amount of binding, or the like, of the target antigen to the solid phase antibody that captures the target antigen is determined by surface plasmon resonance (SPR), surface plasmon-field enhanced fluorescence spectroscopy (SPFS), or the like.

In the biochemical test described above, the liquid sample and the fluorescent labeling liquid are supplied to or collected from the microchannel by dispensation or aspiration using a pipette. Moreover, there are cases where the channel interior is cleaned by a cleaning liquid supplied to the microchannel before the reaction starts or alter the individual liquids are collected. In this case, the cleaning liquid is also supplied to or collected from the microchannel by dispensation or aspiration using a pipette.

CITATION LIST

Patent Literature

Patent Literature 1: JP 2013-185967 A

SUMMARY OF INVENTION

Technical Problem

While, as described above, the biochemical testing apparatus using an analysis chip sequentially supplies a liquid sample, a fluorescent labeling liquid, a cleaning liquid or the like to be used in a biochemical reaction to the microchannel and collects the liquids after a certain period of time, it is difficult to completely collect each of the liquids from the microchannel. For example, Patent Literature 1 discloses a biochemical testing apparatus that inserts a nozzle into an insertion hole of a test chip (hereinafter also referred to as an analysis chip) deeper than a level at the time of liquid delivery so as to collect the liquid as completely as possible from the channel at the time of liquid collection. There is a case, however, a minute amount of liquid remains in the channel even with the use of the biochemical testing apparatus of Patent Literature 1.

Moreover, it is difficult to perform appropriate liquid delivery with a resistance of the channel in a state where the channel is not hermetically sealed when the liquid is supplied to the microchannel, and thus, there is a need to bring a pipette tip 4001 into contact with an insertion hole hermetic seal 3111 as illustrated in FIG. 7A for example, so as to hermetically seal a pipette tip insertion hole 3101. Accordingly, when the pipette tip 4001 is lowered for liquid delivery for a succeeding process or the liquid for the succeeding process is injected into the pipette tip insertion hole 3101 in a state where the pipette tip insertion hole 3101 is hermetically sealed while a liquid 10 of the preceding process remains in a microchannel 3100, a pressure is applied to the interior of the pipette tip insertion hole 3101 to press a residual liquid 10 in the preceding process out toward the downstream side of the microchannel 3100 (refer to FIG. 7B). Subsequently, when liquid delivery of the succeeding process is started in a state of FIG. 7B, a bubble 20 is sandwiched between the liquid of the succeeding process and the residual liquid 10 of the preceding process, so as to be carried toward the downstream side of the microchannel 3100 together with the liquid of the succeeding process (refer to FIG. 7C).

As described above, when the bubble 20 continues to move toward the downstream side of the microchannel 3100, the bubble 20 might come in contact with and adhere to the antigen capture membrane as a reaction field fixed inside the microchannel. As illustrated in FIGS. 8A and 8B, adhesion of the bubble 20 to the antigen capture membrane can be a cause of inhibiting processes such as binding of the target antigen 13 to the solid phase antibody 12 (FIG. 8A), binding of the fluorescent labeling antibody 14 to the target antigen 13 captured by the solid phase antibody 12 (FIG. 8B), and generation of surface plasmon excitation fluorescence, leading to a failure in achieving accurate measurement.

The present invention has been made in view of these situations. According to the present invention, it is possible to achieve liquid delivery in a succeeding step without generation of bubbles even with the residual liquid of the preceding process in the channel. This makes it possible to perform accurate and stable measurements without inhibiting the progress of biochemical reactions or generation of surface plasmon excitation fluorescence by bubbles.

Solution to Problem

A liquid delivery method according to the present invention is a liquid delivery method for supplying a liquid from a nozzle inserted in a liquid delivery portion to a microchannel connected to the liquid delivery portion, the liquid delivery method including: a first step of supplying a first liquid into the microchannel; a second step of collecting the first liquid supplied into the microchannel from within the microchannel; a third step of dispensing a first amount of a second liquid into the liquid delivery portion in a state where the liquid delivery portion is not hermetically sealed; and a fourth step of initially dispensing the first amount of the second liquid and then dispensing a second amount of the second liquid into the liquid delivery portion in a state where the liquid delivery portion is hermetically sealed to supply the second liquid into the microchannel.

A liquid delivery apparatus according to the present invention is a liquid delivery apparatus that detachably mounts an analysis chip having a liquid delivery portion and a microchannel connected with the liquid delivery portion and supplies a liquid from a nozzle inserted to the liquid delivery portion to the microchannel, the liquid delivery apparatus including a liquid delivery controller that performs a procedure including supplying a first liquid into the microchannel, collecting the first liquid from within the microchannel, then, dispensing a first amount of a second liquid into the liquid delivery portion in a state where the liquid delivery portion is not hermetically sealed, and after the first amount of the second liquid has been dispensed, dispensing a second amount of the second liquid into the liquid delivery portion in a state where the liquid delivery portion is hermetically sealed to supply the second liquid into the microchannel.

An analyzer according to the present invention is an analyzer that detachably mounts an analysis chip having a liquid delivery portion and a microchannel connected with the liquid delivery portion, the analyzer including: a liquid delivery unit that is provided to supply a liquid to the microchannel from a nozzle inserted to the liquid delivery unit and performs a procedure including supplying a first liquid into the microchannel, collecting the first liquid from within the microchannel, then, dispensing a first amount of a second liquid into the liquid delivery portion in a state where the liquid delivery portion is not hermetically sealed, and after the first amount of the second liquid has been dispensed, dispensing a second amount of the second liquid into the liquid delivery portion in a state where the liquid delivery portion is hermetically sealed to supply the second liquid into the microchannel; and a detecting unit that detects a result of reaction of a reaction field fixed inside the microchannel.

Advantageous Effects of Invention

According to the present invention, it is possible to achieve liquid delivery in a succeeding step without generation of bubbles even with the residual liquid of the preceding process in the channel. This enables stable measurement while suppressing inhibition of each of processes of reaction and measurement by bubbles.

BRIEF DESCRIPTION OF DRAWINGS

FIG. 5 is a flowchart illustrating a procedure of a biochemical test.

DESCRIPTION OF EMBODIMENTS

Hereinafter, an embodiment of the present invention will be described in detail with reference to the drawings. The present embodiment relates to a biochemical testing apparatus that detects binding of a target antigen by surface plasmon-field resonance enhanced fluorescence spectroscopy (SPFS).

(Outline of Biochemical Testing Apparatus)

Figure 1:
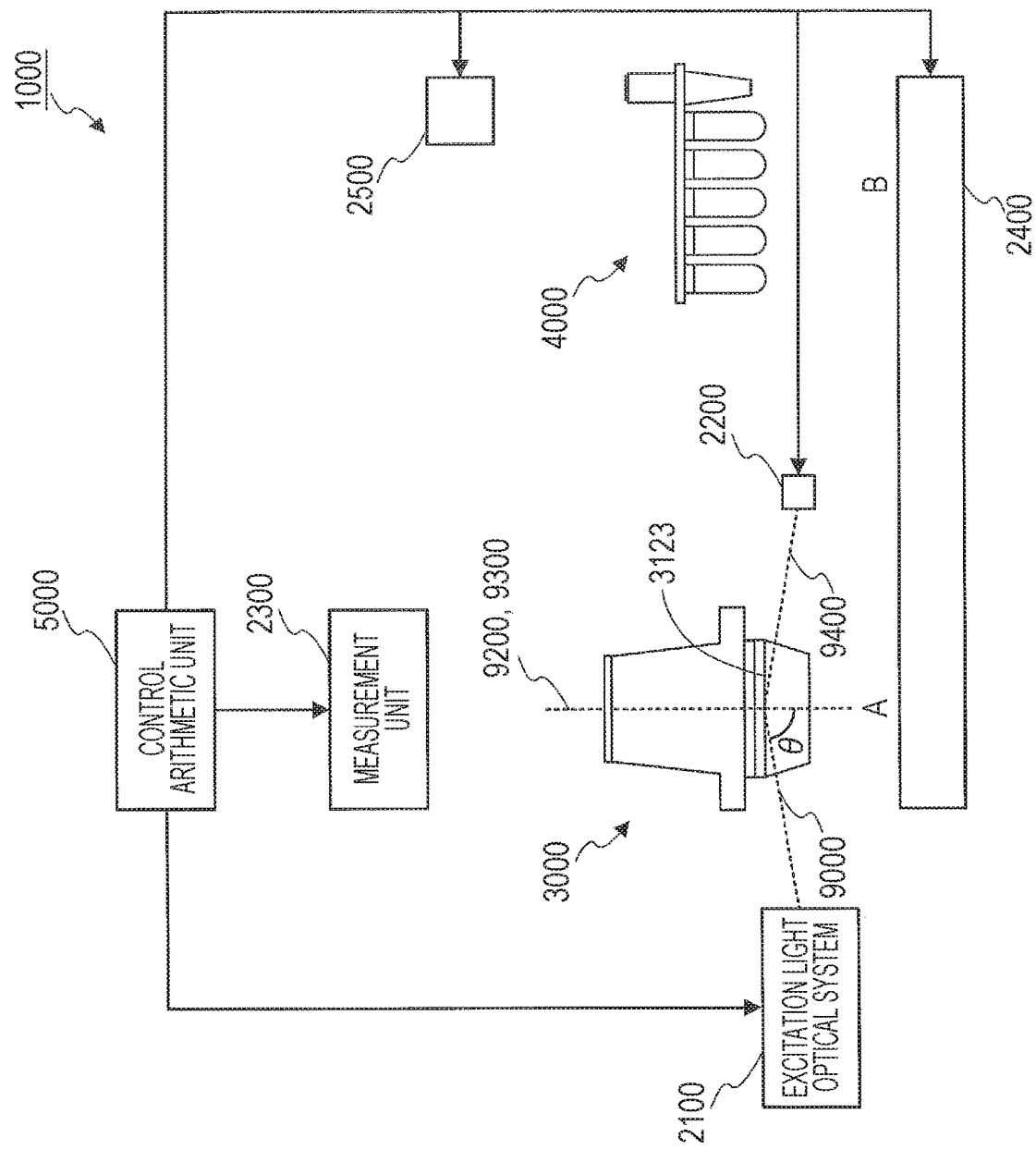
FIG. 1 is a schematic diagram illustrating a configuration of a biochemical testing apparatus.

FIG. 1 is a schematic diagram illustrating a configuration of a biochemical testing apparatus.

As illustrated in FIG. 1, a biochemical testing apparatus 1000 includes an excitation light optical system 2100, a measurement unit 2300, a photodiode 2200, a conveyance mechanism 2400, a pump unit 2500, an analysis chip 3000, a reagent chip 4000, and a control arithmetic unit 5000.

The excitation light optical system 2100 includes a laser diode as a light source and emits excitation light 9000 so as to set an incident angle on a reflection surface 3123 of the analysis chip 3000 to an angle $\theta$.

The measurement unit 2300 includes a photomultiplier tube as a light receiving element and is arranged on an optical path of surface plasmon excitation fluorescence 9200 and measures light amounts of the surface plasmon excitation fluorescence 9200 and scattered light 9300. The light amount of the surface plasmon excitation fluorescence 9200 is used to determine the presence or absence of binding of the target antigen or the amount of binding of the target antigen. The light amount of the scattered light 9300 is used to detect an incident angle (resonance angle) $\theta r$ that maximizes an electric field enhancement degree described below. In this case, the angle $\theta$ as the incident angle that maximizes the light amount of the scattered light 9300 is detected as the resonance angle $\theta r$. Alternatively, the resonance angle $\theta r$ may be detected using the following photodiode 2200. In that case, there is no need to detect the resonance angle $\theta r$ using the light amount of the scattered light 9300.

The photodiode 2200 is arranged on the optical path of reflected light 9400 of the excitation light 9000 to measure the light amount of the reflected light 9400. The light amount of the reflected light 9400 is used for detecting the resonance angle $\theta r$. In this case, the angle $\theta$ of the incident angle that minimizes the light amount of the reflected light 9400 is detected as the resonance angle $\theta r$. When the resonance angle $\theta r$ is not to be detected by the light amount of the reflected light 9400, the photodiode 2200 may be omitted and replaced by a light absorber or the like.

The analysis chip 3000 is attached to the conveyance mechanism 2400. The conveyance mechanism 2400 allows the analysis chip 3000 to reciprocate between a reaction position B during the progress of reaction and a measurement position A on a measurement optical path. The pump unit 2500 includes a moving mechanism to move the pipette tip to a predetermined position and a liquid delivery mechanism that performs aspiration and dispensation of a liquid. The reagent chip 4000 includes liquid containers that contain individual liquids used in biochemical reactions.

The control arithmetic unit 5000 includes a control arithmetic block group that controls operation of each of the above-described components.

(Analysis Chip)

Figure 2:
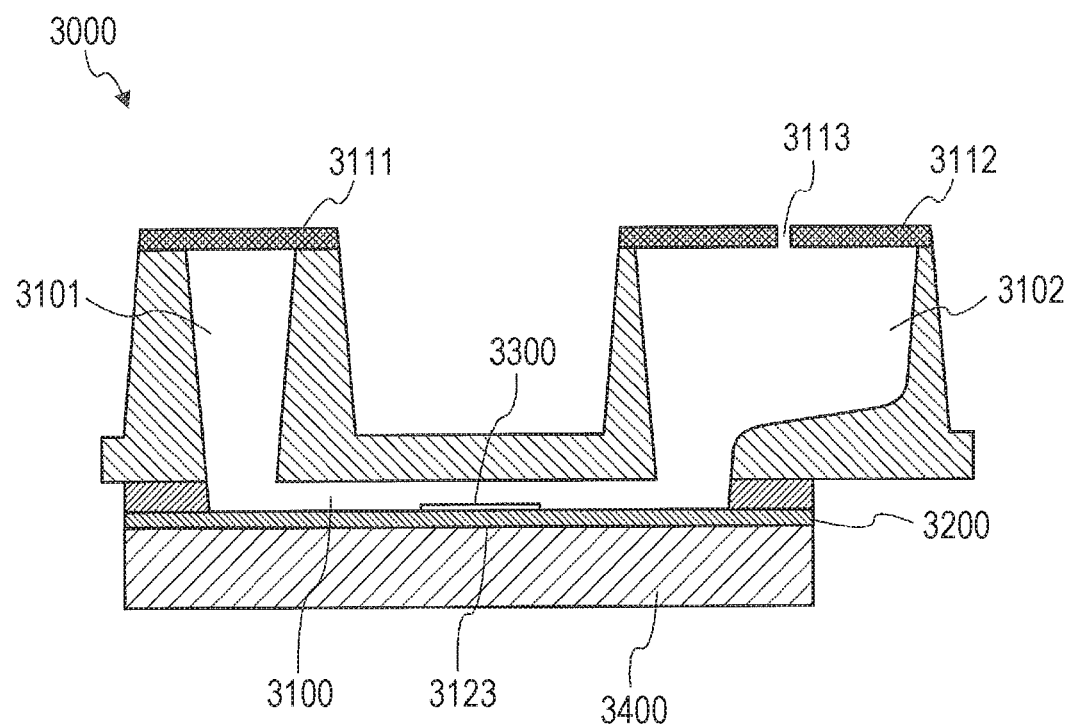
FIG. 2 is a cross-sectional view of an analysis chip.

FIG. 2 is a cross-sectional view of the analysis chip 3000.

As illustrated in FIG. 2, the microchannel 3100 is formed in the analysis chip 3000. One end of the microchannel 3100 is connected to the pipette tip insertion hole 3101 (liquid delivery part) to which the pipette tip is inserted, while the other end is connected to a liquid reservoir 3102 to receive the liquid in reciprocating the liquid in the channel. Each of an insertion hole hermetic seal 3111 and a liquid reservoir seal 3112 are respectively attached to each of openings of the pipette tip insertion hole 3101 and the liquid reservoir 3102, not connected to the microchannel 3100. While the opening of the pipette tip insertion hole 3101 not connected to the microchannel 3100 is hermetically sealed by attaching the insertion hole hermetic seal 3111, the liquid reservoir seal 3112 has a vent 3113. When the pipette tip is first inserted to the pipette tip insertion hole 3101, the pipette tip pierces the insertion hole hermetic seal 3111 to be inserted.

An antigen capture membrane 3300 to be a reaction field is fixed inside the microchannel 3100. During the progress of the biochemical reaction, liquids such as a liquid sample, a fluorescent labeling liquid or a cleaning liquid are sequentially supplied to the microchannel 3100 by the pump unit 2500 and brought into contact with the antigen capture membrane 3300. Liquid delivery control for each of the liquids will be described below.

A bottom surface of the analysis chip 3000 includes a conductor film 3200 and a prism 3400 provided for generating surface plasmon resonance. The conductor film 3200 is a thin film formed of gold. Alternatively, the conductor film 3200 may be formed of a metal such as silver, copper, aluminum, or an alloy containing these metals. The prism 3400 is a dielectric medium formed of a material transparent to the excitation light 9000.

(Reagent Chip)

Figure 3:
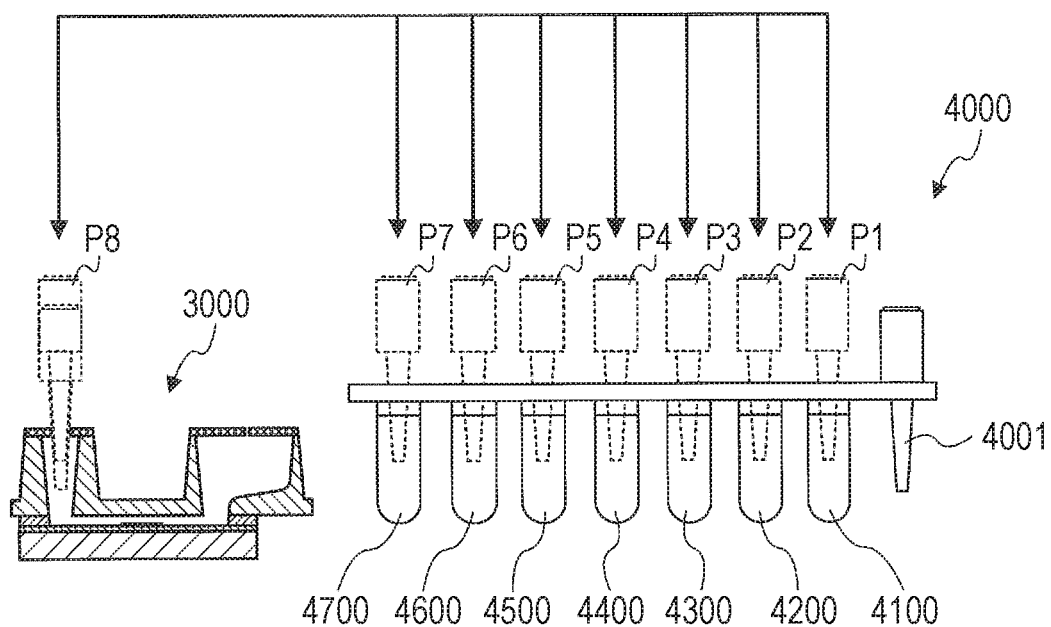
FIG. 3 is an explanatory view for illustrating a reagent chip.

FIG. 3 is an explanatory diagram for illustrating the reagent chip 4000.

As illustrated in FIG. 3, the reagent chip 4000 includes a cleaning liquid container 4100, a specimen container 4200, a dilution container 4300, a liquid sample container 4400, a fluorescent labeling liquid container 4500, a measurement liquid container 4600, and a waste liquid container 4700. Each of the liquid containers 4100 to 4700 respectively contains a cleaning liquid, a specimen, a dilution, a liquid sample, a fluorescent labeling liquid, a measurement liquid, and a waste liquid. In advancing the biochemical reaction, each of the liquids is supplied from each of the liquid containers 4100 to 4600 to the microchannel 3100 of the analysis chip 3000 by the pump unit 2500. Moreover, the spent liquid collected from the microchannel 3100 is stored in the waste liquid container 4700.

When the liquid is supplied to the microchannel 3100, the pipette tip 4001 is attached to the pump unit 2500 under the control of the control arithmetic unit 5000. The pump unit 2500 moves the pipette tip to a predetermined position (any of positions P1 to P6), lowers the pipette tip into a predetermined liquid container, and aspirates a predetermined liquid. For example, in the case of supplying the liquid sample to the microchannel 3100, the pump unit 2500 moves the pipette tip to the position P4 above the liquid sample container 4400, lowers the pipette tip so as to be immersed in the liquid sample to aspirate the liquid sample. Next, after aspirating a predetermined amount of liquid, the pump unit 2500 raises the pipette tip, moves the pipette tip to the position P8 above the pipette tip insertion hole 3101 of the analysis chip 3000, and inserts the pipette tip to the pipette tip insertion hole 3101. Note that an insertion depth of the pipette tip to the pipette tip insertion hole 3101 is adjusted stepwise and controlled so as to dispense the liquid for each of the steps. Details of this liquid delivery method will be described below.

In a case of collecting the liquid from the microchannel 3100, the pump unit 2500 aspirates the liquid inside the channel. After most of the liquid inside the channel is aspirated, the pump unit 2500 raises the pipette tip to move to the position P7 above the waste liquid container 4700 of the reagent chip 4000 under the control of the control arithmetic unit 5000. Next, the pump unit 2500 lowers the pipette tip into the waste liquid container 4700 and dispenses all of the aspirated liquid.

(Control Arithmetic Unit)

Figure 4:
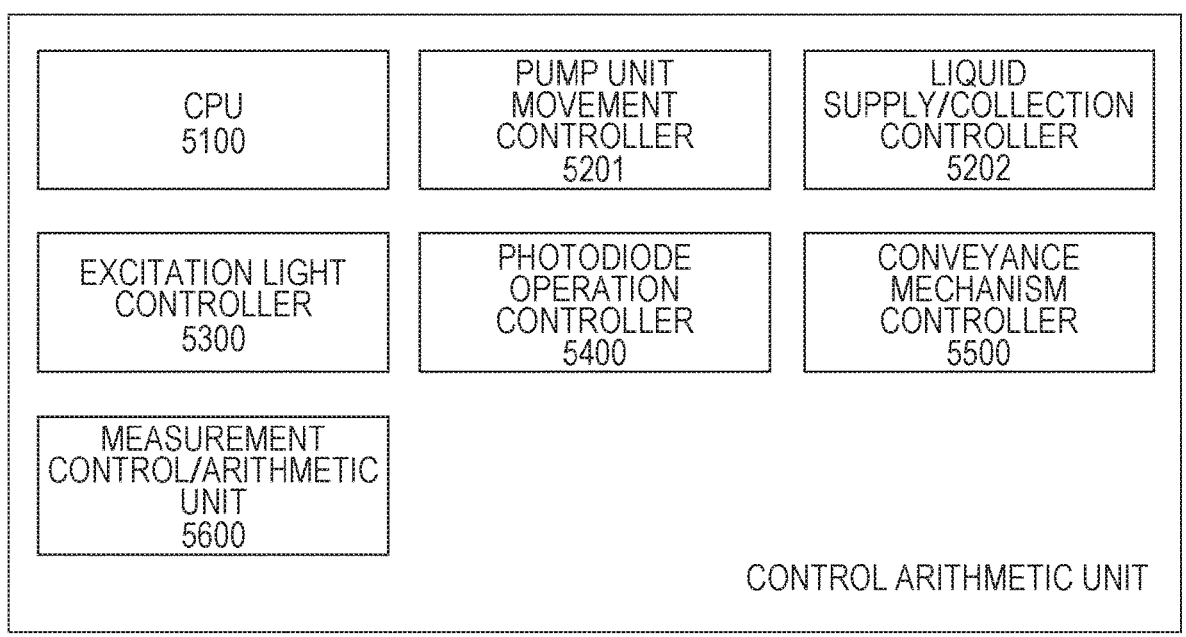
FIG. 4 is a block diagram of a control arithmetic unit.

FIG. 4 is a block diagram of the control arithmetic unit.

As illustrated in FIG. 4, the control arithmetic unit 5000 includes a CPU 5100, an excitation light controller 5300, a photodiode operation controller 5400, a conveyance mechanism controller 5500, a pump unit movement controller 5201, a liquid supply/collection controller 5202, and a measurement control/arithmetic unit 5600.

The CPU controls the entire biochemical test. The excitation light controller controls emission of excitation light. The photodiode operation controller controls operation of the photodiode 2200. The conveyance mechanism controller controls the conveyance mechanism 2400 to convey the analysis chip 3000 to a predetermined position. The pump unit movement controller determines the position and the height of the pipette tip and controls the moving mechanism of the pump unit 2500 so as to move the pipette tip to the predetermined position and height. The liquid supply/collection controller determines the operation of dispensation or aspiration of liquid, and controls the liquid delivery mechanism of the pump unit 2500 so as to disperse or aspirate a predetermined amount of liquid. The measurement control/arithmetic unit performs control related to measurement, such as measurement of the light amount of surface plasmon excitation fluorescence.

(Outline of Biochemical Test)

The biochemical test is a method of capturing a target antigen as a detection target by a biochemical reaction, attaching a fluorescent label to the captured target antigen, and determining the presence or absence of the detection target or captured amount, or the like, from the light amount of fluorescence attributed to the attached fluorescent label. FIG. 5 is a flowchart illustrating a procedure of a biochemical test. Hereinafter, a procedure of a biochemical test will be described with reference to FIG. 5.

At a start of the test, the measurement liquid is first supplied to the microchannel 3100 (step S101). At this time, the analysis chip 3000 is arranged at the reaction position B. The measurement liquid also serves as a cleaning liquid. As described above, the antigen capture membrane 3300 to be a reaction field to which the solid phase antibody is immobilized is fixed in the microchannel 3100. The antigen capture membrane 3300 has coating of a protective layer provided to maintain a solid phase antibody capture capability for a long period. Therefore, after the measurement liquid is supplied to the microchannel 3100, the measurement liquid is caused to reciprocate within the channel to remove the protective layer. The cleaning described above may be performed by using a dedicated cleaning liquid instead of the measurement liquid. In a case where the microchannel 3100 and the antigen capture membrane 3300 are clean and the preservation protective layer or the like is not coated on the antigen capture membrane 3300, there is no need to perform cleaning.

After the removal the protective layer, succeeding enhancement measurement is performed while the measurement liquid is filled in the microchannel 3100 without being collected (step S102). At this time, the analysis chip 3000 is arranged at the measurement position A on the measurement optical path, the angle θ as the incident angle that maximizes the light amount of the scattered light 9300 or the angle θ as the incident angle that minimizes the light amount of the reflected light 9400 is detected as the resonance angle θr. After completion of the enhancement measurement, the measurement liquid is collected from the microchannel 3100 by aspiration by the pump unit 2500 so as to be stored in the waste liquid container 4700 of the reagent chip 4000.

Next step to perform is a primary reaction to bind the target antigen with the solid phase antibody (step S103). At this time, the analysis chip 3000 is arranged at the reaction position B, and the liquid sample is supplied to the microchannel 3100. The liquid sample is obtained by diluting the specimen collected directly from an examinee with dilution. When the sample fluid is filled in the microchannel 3100, the liquid sample comes in contact with the antigen capture membrane 3300, and the target antigen contained in the liquid sample binds to the solid phase antibody immobilized on the antigen capture membrane 3300 and is then captured. After the lapse of a sufficient time for the reaction, the liquid sample is collected from the microchannel 3100 to be stored in the waste liquid container 4700 of the reagent chip 4000.

Next, the inside of the channel is cleaned (step S104). In order to remove nonspecifically adsorbed target antigens, a cleaning liquid is supplied to the microchannel 3100 and is reciprocated to clean the microchannel 3100. After completion of cleaning, the cleaning liquid is collected from the microchannel 3100 to be stored in the waste liquid container 4700 of the reagent chip 4000.

Next, a secondary reaction for fluorescent labeling is performed (step S105). In this case, a fluorescent labeling liquid is supplied to the microchannel 3100. When the fluorescent labeling liquid is filled in the microchannel 3100, the fluorescent labeling liquid and the antigen capture membrane 3300 come into contact with each other, and the fluorescent labeling antibody contained in the fluorescent labeling liquid binds to the captured target antigen, so as to attach a fluorescent label to the captured target antigen. After the lapse of a sufficient time for the reaction, the fluorescent labeling liquid is collected from the microchannel 3100 to be stored in the waste liquid container 4700 of the reagent chip 4000. Thereafter, the cleaning liquid is supplied into the microchannel 3100, and the inside of the channel is cleaned (step S106) similarly to step S104.

Finally, in order to determine the presence or absence of binding or the amount of binding of the target antigen to the solid phase antibody, the intensity of the fluorescent label attached to the target antigen, that is, the light amount of fluorescence is measured (step S107). At this time, with the analysis chip 3000 being arranged at the measurement position A, the excitation light 9000 from the excitation light optical system 2100 is emitted to the reflection surface 3123 of the analysis chip 3000. The excitation light 9000 is reflected by the reflection surface 3123, and at the time of reflection, an evanescent wave leaks from the reflection surface 3123 to the conductor film 3200 side. The electric field of the leaking evanescent wave resonates with the surface plasmon of the conductor film 3200 and is enhanced. The enhanced electric field excites the fluorescent label attached to the target antigen captured by the antigen capture membrane 3300. From the excited fluorescent label, surface plasmon excitation fluorescence 9200 is emitted. The measurement unit 2300 measures the light amount of the surface plasmon excitation fluorescence 9200 and determines the presence or absence or the amount of binding of the target antigen.

In the above-described biochemical test procedure, particularly in the primary reaction in step S103, the secondary reaction in step S105, and the light amount measurement in step S107, bubbles attached to the antigen capture membrane 3300 might hinder the progress of individual processes, specifically, by suppressing the reaction or scattering of the excitation fluorescence, leading to an occurrence of errors in measurement results. Accordingly, the liquid delivery is controlled to suppress the generation of bubbles as described below so as to achieve accurate and stable measurement.

(Liquid Delivery Method)

FIGS. 6A to 6E are schematic diagrams illustrating a liquid delivery method.

As illustrated in FIGS. 6A to 6E, when a liquid is supplied to the microchannel 3100 by this liquid delivery method, the liquid is dispensed at different insertion depths with two different stages.

Figure 6A:
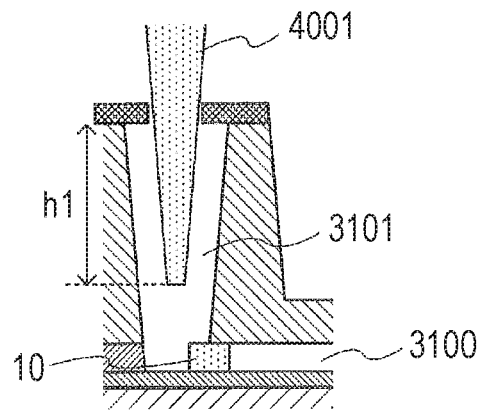
FIGS. 6A to 6E are schematic diagrams illustrating a liquid delivery method.
Figure 6B:
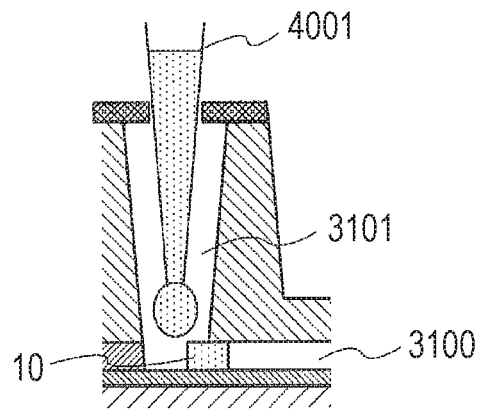
Figure 6C:
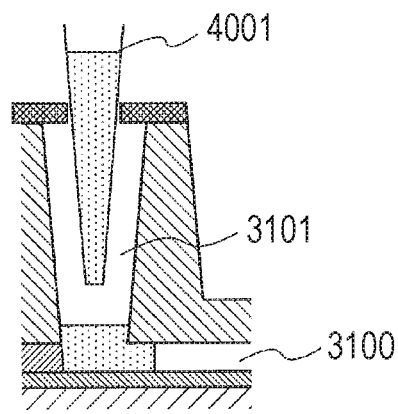

As illustrated in FIG. 6A, the pipette tip 4001 is inserted to a relatively shallow first insertion depth h1 so as not to hermetically seal the pipette tip insertion hole 3101 in a first stage liquid delivery. This configuration ensures an air escape between the pipette tip 4001 and the insertion hole hermetic seat 3111. Next, first liquid dispensation is performed at the first insertion depth h1. As illustrated in FIG. 6B, since the air escape is ensured in this state, dispensation of the liquid would apply no pressure to the inside of the pipette tip insertion hole 3101, and thus, the residual liquid 10 in the preceding process is not pushed out toward the downstream side of the microchannel 3100. Moreover, as illustrated in FIG. 6C, the dispensed liquid is integrated with the residual liquid 10 in the preceding process, so as to be stored in the pipette tip insertion hole 3101. This prevents bubbles from being sandwiched between the dispensed liquid and the residual liquid in the preceding process, leading to suppression of the generation of bubbles. In the first stage liquid delivery, approximately 35 µL of liquid is dispensed so as to allow an end of the pipette tip 4001 to be positioned at a liquid surface or below when the pipette tip 4001 is inserted to a second insertion depth h2 to be described below.

Figure 6D:
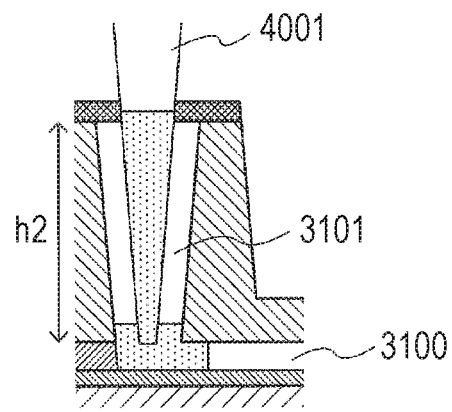
Figure 6E:
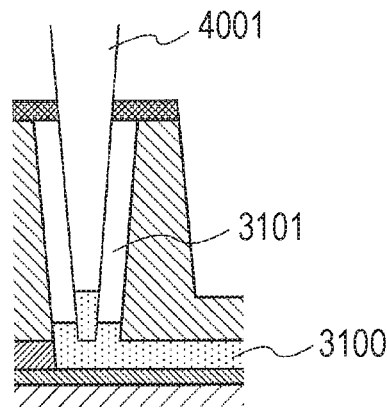
Figure 7A:
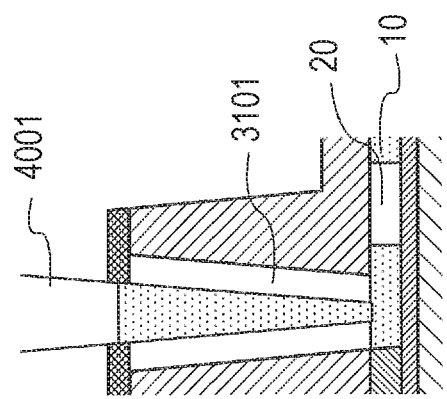
FIGS. 7A to 7C are schematic diagrams illustrating a mechanism related to bubble formation.
Figure 7B:
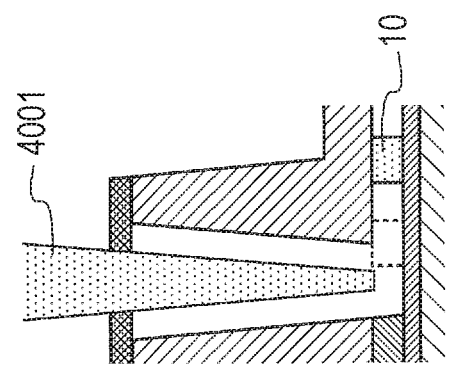
Figure 7C:
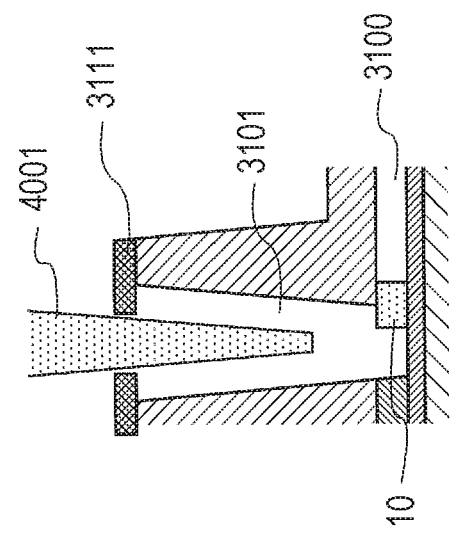
Figure 8A:
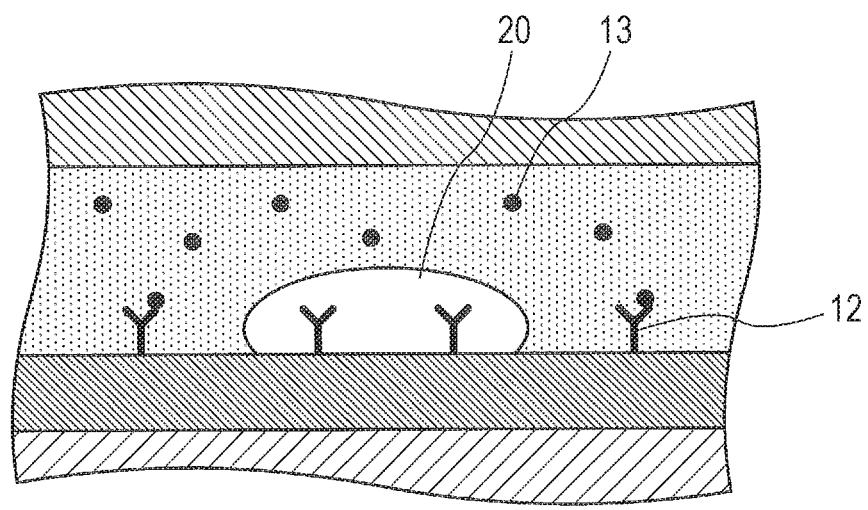
FIGS. 8A and 8B are explanatory diagrams illustrating a state where bubbles adhere to an antigen capture membrane.
Figure 8B:
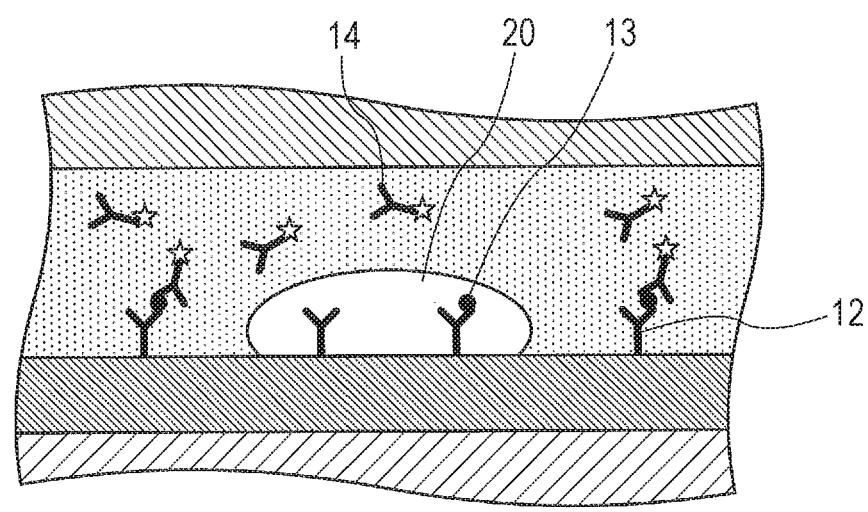

Next, under the control of the control arithmetic unit 5000, the pipette tip 4001 is inserted to the second insertion depth h2 deeper than the first insertion depth h1 as illustrated in FIG. 6D, so as to come into contact with the insertion hole hermetic seal 3111 and hermetically seal the pipette tip insertion hole 3101. This leaves no air escape at the pipette tip insertion hole 3101 side. Next, dispensing the liquid in this state would apply pressure to the inside of the channel, making it possible to supply the liquid into the microchannel 3100 as illustrated in FIG. 6E. In a second stage liquid delivery, about 45 µL of liquid is dispensed to allow reciprocation of the liquid throughout the microchannel 3100. Thereafter, under the control of the control arithmetic unit 5000, the pump unit 2500 aspirates and then dispenses 70 µL of the liquid and to allow reciprocation of the liquid in the channel, so as to allow the liquid to be sufficiently in contact with the antigen capture membrane 3300.

As described above, the present liquid delivery method controls liquid delivery so as to first inject a portion of the liquid into the pipette tip insertion hole 3101 while ensuring the air permeability, thereafter injecting remaining liquid with the pipette tip insertion hole 3101 hermetically sealed, while supplying the liquid into the microchannel 3100. According to this liquid delivery method, it is possible to achieve liquid delivery without generation of bubbles.

While the present embodiment is a case where the liquid delivery is performed in two stages depending on the presence or absence of air permeability of the pipette tip insertion hole 3101, there is no need to limit the liquid delivery to two stages. It would be sufficient to be able to inject the liquid integrated with the residual liquid of the preceding process in a state where air permeability of the pipette tip insertion hole 3101 is ensured in order to eliminate the risk of bubble generation. It would be sufficient, thereafter, to be able to supply the liquid to the microchannel 3100 while suppressing recurrence of generation of bubbles due to the liquid delivery operation, or the like. For example, the liquid delivery may be performed in two or more stages or the liquid may be gradually dispensed while lowering the pipette tip without dividing the liquid delivery into different stages.

This application claims priority based on Japanese Patent Application No. 2015-214782 filed on Oct. 30, 2015. The contents described in the application specification and drawings are all incorporated herein by reference.

REFERENCE SIGNS LIST

10 Liquid (residual liquid)
12 Solid phase antibody
13 Target antigen
14 Fluorescent labeling antibody
20 Bubble
1000 Biochemical testing apparatus
2100 Excitation light optical system
2200 Photodiode
2300 Measurement unit
2400 Conveyance mechanism
2500 Pumping unit
3000 Analysis chip
3100 Microchannel
3101 Pipette tip insertion hole
3102 Liquid reservoir
3111 Insertion hole hermetic seal
3112 Liquid reservoir seal
3113 Vent
3123 Reflection surface
3200 Conductor film
3300 Antigen capture membrane
3400 Prism
4000 Reagent chip
4001 Pipette tip
4100 Cleaning liquid container (liquid container)
4200 Specimen container (liquid container)
4300 Dilution (liquid container)
4400 Liquid sample container (liquid container)
4500 Fluorescent labeling liquid container (liquid container)
4600 Measurement liquid container (liquid container)
4700 Waste liquid container (liquid container)
5000 Control arithmetic unit
5100 CPU
5201 Pump unit movement controller
5202 Liquid supply/collection controller
5300 Excitation light controller
5400 Photodiode operation controller
5500 Conveyance mechanism controller
5600 Measurement control/calculation unit
9000 Excitation light
9200 Surface plasmon excitation fluorescence
9300 Scattered light
9400 Reflected light

The invention claimed is:

1. A liquid delivery method for supplying a liquid from a nozzle inserted in a liquid delivery part to a microchannel connected to the liquid delivery part, the liquid delivery method comprising:
supplying a first liquid into the microchannel;
collecting the first liquid supplied into the microchannel from within the microchannel;
dispensing a first amount of a second liquid, which is different from the first liquid, into the liquid delivery part in a state in which the liquid delivery part is not hermetically sealed; and
after having dispensed the first amount of the second liquid into the liquid delivery part, dispensing a second amount of the second liquid into the liquid delivery part in a state in which the liquid delivery part is hermetically sealed, to supply the second liquid into the microchannel.

2. The liquid delivery method according to claim 1, wherein the liquid is supplied to the microchannel by inserting the nozzle into the liquid delivery part through a hermetic seal attached to an opening of the liquid delivery part.

3. The liquid delivery method according to claim 2, wherein the nozzle is arranged at a first position being not closely in contact with the hermetic seal when the first amount of the second liquid is dispensed into the liquid delivery part, and the nozzle is arranged at a second position being in close contact with the hermetic seal when the second amount of the second liquid is dispensed into the liquid delivery part.

4. The liquid delivery method according to claim 3, wherein, when the second amount of the second liquid is dispensed, an end of the nozzle is arranged at or below a liquid surface of the liquid inside the liquid delivery part.

5. The liquid delivery method according to claim 2, wherein:
the first amount of the second liquid is dispensed while moving the nozzle from a first position not being in close contact with the hermetic seal to a second position being in close contact with the hermetic seal, after the first liquid is collected from within the microchannel; and
the second amount of the second liquid is dispensed in a state in which the nozzle is in close contact with the hermetic seal.

6. The liquid delivery method according to claim 5, wherein, when the second amount of the second liquid is dispensed, an end of the nozzle is arranged at or below a liquid surface of the liquid inside the liquid delivery part.

7. The liquid delivery method according to claim 2, wherein, when the second amount of the second liquid is dispensed, an end of the nozzle is arranged at or below a liquid surface of the liquid inside the liquid delivery part.

8. The liquid delivery method according to claim 1, wherein, when the second amount of the second liquid is dispensed, an end of the nozzle is arranged at or below a liquid surface of the liquid inside the liquid delivery part.

9. The liquid delivery method according to claim 1, wherein the second amount of the second liquid is different from the first amount of the second liquid.

10. The liquid delivery method according to claim 9, wherein the second amount of the second liquid is greater than the first amount of the second liquid.

11. A liquid delivery apparatus onto which an analysis chip is detachably mountable, said analysis chip having a liquid delivery part and a microchannel connected with the liquid delivery part, the liquid delivery apparatus comprising:
a nozzle which is removably insertable into the liquid delivery part of the analysis chip; and
a liquid delivery controller that controls the nozzle to perform a procedure including supplying a first liquid into the microchannel, collecting the first liquid from within the microchannel, disposing of the first liquid, then, dispensing a first amount of a second liquid, which is different from the first liquid, into the liquid delivery part in a state in which the liquid delivery part is not hermetically sealed, and after the first amount of the second liquid has been dispensed into the liquid delivery part, dispensing a second amount of the second liquid into the liquid delivery part in a state in which the liquid delivery part is hermetically sealed, to supply the second liquid into the microchannel.

12. The liquid delivery apparatus according to claim 11, further comprising a nozzle movement controller that performs control to move the nozzle to a predetermined position.

13. The liquid delivery apparatus according to claim 12, wherein the nozzle movement controller performs control to insert the nozzle into the liquid delivery part through a hermetic seal attached to an opening of the liquid delivery part.

14. The liquid delivery apparatus according to claim 13, wherein, at a time of bringing the liquid delivery part into the hermetically sealed state, the nozzle movement controller performs control to bring the nozzle into close contact with the hermetic seal to hermetically seal the liquid delivery part.

15. The liquid delivery apparatus according to claim 14, wherein the nozzle movement controller performs control of the nozzle so as to set an end of the nozzle to be arranged at or below a liquid surface of the liquid inside the liquid delivery part, when dispensing the second amount of the second liquid.

16. The liquid delivery apparatus according to claim 13, wherein the nozzle movement controller performs control of the nozzle so as to set an end of the nozzle to be arranged at or below a liquid surface of the liquid inside the liquid delivery part, when dispensing the second amount of the second liquid.

17. The liquid delivery apparatus according to claim 12, wherein the nozzle movement controller performs control of the nozzle so as to set an end of the nozzle to be arranged at or below a liquid surface of the liquid inside the liquid delivery part, when dispensing the second amount of the second liquid.

18. An analyzer onto which an analysis chip is detachably mountable, said analysis chip having a liquid delivery part and a microchannel connected with the liquid delivery part, the analyzer comprising:
  a nozzle which is removably insertable into the liquid delivery part of the analysis chip; and
  a liquid delivery controller that controls the nozzle to perform a procedure including supplying a first liquid into the microchannel, collecting the first liquid from within the microchannel, disposing of the first liquid, then, dispensing a first amount of a second liquid, which is different from the first liquid, into the liquid delivery part in a state in which the liquid delivery part is not hermetically sealed, and after the first amount of the second liquid has been dispensed into the liquid delivery part, dispensing a second amount of the second liquid into the liquid delivery part in a state in which the liquid delivery part is hermetically sealed, to supply the second liquid into the microchannel; and
  a detector that detects a result of reaction of a reaction field fixed inside the microchannel.

19. The analyzer according to claim 18, further comprising an incident light emitter that emits incident light,
  wherein the detector comprises an optical detector that detects one of reflected light and excitation light emitted from the reaction field.

* * * * *